United States Patent [19]

Brownfield

[11] Patent Number: 5,681,283
[45] Date of Patent: Oct. 28, 1997

[54] DEVICE FOR PAINLESS INSERTION OF NEEDLE FOR NEEDLE INJECTED MEDICATION

[76] Inventor: Carroll James Brownfield, 519 W. Nelda, Houston, Tex. 77037

[21] Appl. No.: 494,765

[22] Filed: Feb. 27, 1995

[51] Int. Cl.$^6$ ..................................................... A61M 5/20
[52] U.S. Cl. ........................ 604/136; 604/131; 604/192; 604/187
[58] Field of Search ........................ 604/192, 131–135, 604/218, 207, 208, 187, 136; 128/919

[56] References Cited

U.S. PATENT DOCUMENTS

| | | | |
|---|---|---|---|
| 4,636,197 | 1/1987 | Chu | 604/131 |
| 4,950,163 | 8/1990 | Zimble | 433/215 |
| 4,950,265 | 8/1990 | Taylor | 606/1 |
| 5,024,662 | 6/1991 | Meno et al. | 604/131 |
| 5,531,696 | 7/1996 | Menes | 604/131 |

Primary Examiner—Vanitha M. Alexander

[57] ABSTRACT

A device to insert hypodermic syringe needles into the skin at such velocity as to render the penetration of said needle undetectable by the body therefore painless for the patient. The device to consist of a sleeve or tube (hereafter called sleeve) and elastic bands, the internal diameter of the sleeve to be slightly larger than the hypodermic syringe barrel in order to act as a guide for the hypodermic syringe barrel, one end of the sleeve is left open the other end is closed off, there being a small hole in the exact center of the closed end the hole is large enough for the needle to pass through but too small for the hypodermic syringe barrel this closed end of the sleeve is enlarged to absorb the shock of the hypodermic syringe barrel as it is stopped by the closed end of the sleeve and has places on the exterior of it for attachment of elastic bands which provide the energy to propel the hypodermic syringe barrel and needle.

1 Claim, 1 Drawing Sheet

DEVICE FOR PAINLESS INSERTION OF NEEDLE FOR NEEDLE INJECTED MEDICATION

FIELD OF INVENTION

This invention is in the field of medication subcutaneously administered.

DESCRIPTION OF THE PRIOR ART

There are various devices for medication injection, hypodermic syringe needles,compressed air or jets.

The instant invention attempts to overcome deficiencies of the prior art by providing a simple,inexpensive device for the general patient population.

SUMMARY OF THE INVENTION

In view of the disadvantages inherent in the known types of injectors now present in the prior art ,expressly being the expense or needle pain of the same.

It is the object of the present invention to provide a method of painless needle injection for subcutaneous medication.

It is the object of the present invention to provide a simple syringe needle injection device.

It is the object of the present invention to provide a inexpensive syringe needle injection device.

In addition it is the object of the present invention to provide such a device that may be self administered.

The operation of the instant invention is based on the fact that a object penetrating the skin at sufficient high velocity will not cause pain sensation.

In operation the syringe is loaded with medication in the usual manner then inserted needle first into the open end of the sleeve, the rubber bands are looped over the finger grips of the syringe and the syringe is drawn back by the finger grips similar to an arrow in a bow, the enlarged shoulder or needle end of the sleeve is placed vertically on the skin at point of injection, the finger grips are released and the syringe driven forward within the sleeve, stopped by a closed end of the sleeve while the needle passes through the small hole to penetrates the skin. The medication injected in the usual manner.

DETAIL DESCRIPTION OF THE DRAWING

Figure 1:
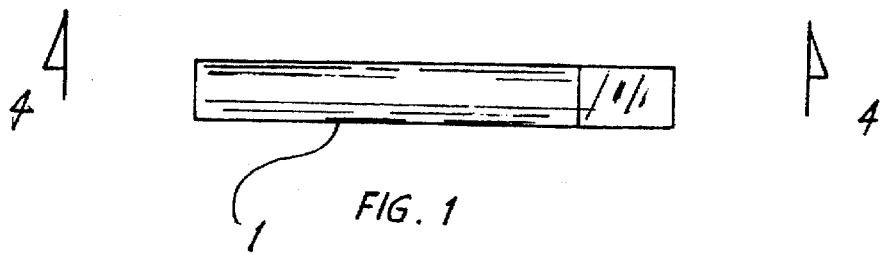
FIG. 1 is a top view of the device.

FIG. 1 is a top view of the device and sleeve(1).

Figure 2:
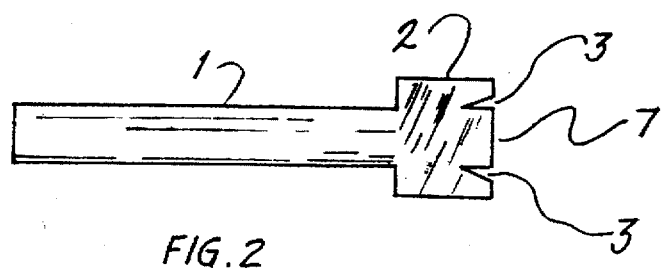
FIG. 2 is side view thereof at the right end of this view is shown the enlarged base portion with tapered slots.

FIG. 2 is side view thereof at the right end of this view is shown the enlarged base portion(2) the base(7) with slots(3) for rubber bands.

Figure 3:
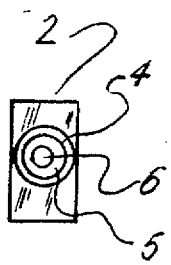
FIG. 3 is left end view of the device showing the sleeve for the hypodermic syringe.

FIG. 3 is left end view of the device showing the sleeve large open end(4) for insertion of hypodermic syringe,the shoulder(5) and the small hole(6) for the syringe needle.

Figure 4:
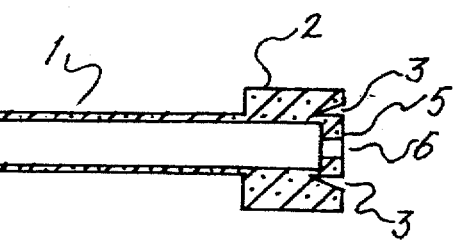
FIG. 4 is a section view looking through the device taken from FIG. 1 showing the sleeve with the shoulder at the end to stop the hypodermic syringe with the small hole thru it for the needle to exit.

FIG. 4 is a section view looking through the device taken from FIG. 1 showing the syringe guide sleeve(1),the large open end(4) the enlarged portion(2) containing shoulder at the end of the sleeve (5) to stop the hypodermic syringe with the small hole(6) through it for the needle to exit,and the slots(3) for rubber bands.

Figure 5:
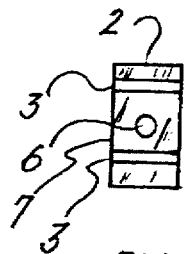
FIG. 5 is right end view or base of the device showing the needle hole and the tapered slots for the rubber bands.

FIG. 5 is right end view of the device showing the needle hole(6) and the slots(3) the base(7) provides a surface of sufficient size to dissipate the force of the syringe after being stopped by the shoulder.

Figure 6:
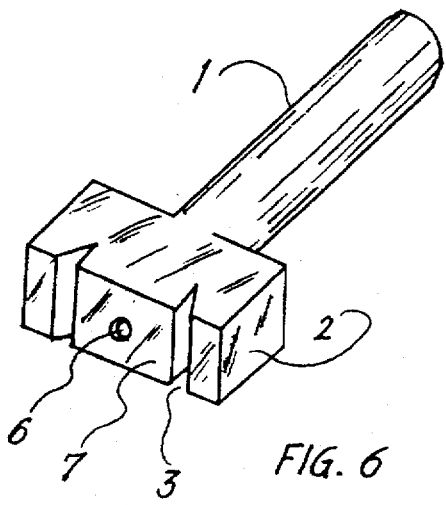
FIG. 6 is a perspective of the device viewed from the FIG. 5 end.

FIG. 6 is a perspective of the device viewed from the FIG. 5 end showing the sleeve(1), rubber band slots(3),needle hole(6),enlarged base(7).

Figure 7:
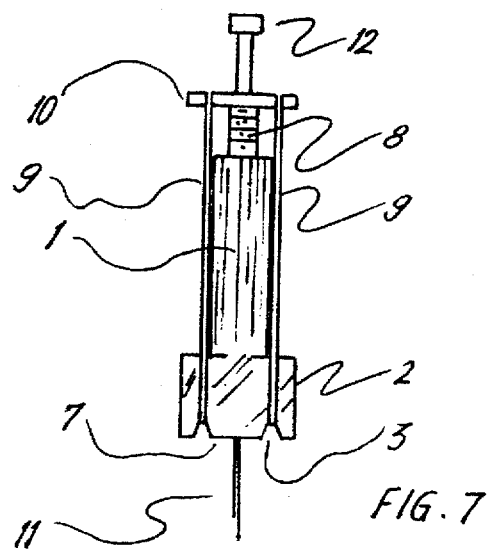
FIG. 7 is an assembly view of the device showing the hypodermic syringe in place with rubber bands looped over syringe finger grips preparatory to arming for injection.

FIG. 7 is an assembly view of the device showing the hypodermic syringe((8) inside the sleeve(1) with rubber bands(9) inserted into slots(3) and looped over syringe finger grips(10) and needle(11) protruding through hole in device base preparatory to arming for injection.

Basically the device is a sleeve(1) with inside diameter sized to guide the hypodermic syringe body which is being driven toward the base(7) by the power of the stretched rubber bands(9) at such velocity that the needle will exit thru the hole(6) and penetrate the skin painlessly. While the syringe body is stopped by the shoulder(5) of the device this energy being absorbed by the enlarged base(7).

The device will be made of ridged material preferable clear plastic by injection molding but may be made of metal or even wood.

Dimensions of the device and size of rubber bands may vary to suit the size and make of syringe.

In use the syringe is loaded with medication as usual, then dropped needle down through large end(4) into the sleeve(1) of the device, the two rubber bands(9) are then looped over the finger grips(10) of the syringe, by grasping the enlarged base portion(2) with the finger and thumb of one hand and the finger grips of the syringe(10) with the thumb and finger of the other hand the syringe(8) is drawn back into the sleeve stretching the rubber bands(9) like an arrow in a bow. Then with the base of the device(7) held firmly but gently against the skin at injection point the syringe finger grips(10) are released shooting the needle(11) into the skin, the medication is then injected by retaining the grip on the enlarged base(2) while using the free hand hooking the fingers under the finger grips(10) and depressing syringe plunger(12) injecting the medication in the usual manner. After injection the device(1) is lifted vertically away from the skin.

Many variations in the present invention are contemplated and included. For example the sleeve and enlarged portion may be fabricated separately or from different materials.

It will be apparent that other modifications and variations of the described embodiment may be effective without departing from the scope or spirit of this invention.

What I claim and desire to have protected by Letters Patent is as follows:

1. A device to insect hypodermic syringe needles into the patient without needle pain comprising: a sleeve with a closed end and a small opening in the center of said closed end said end of the sleeve being enlarged and provided with diametrically opposed slots and rubber bands fitting into said slots wherein, said rubber bands have a preselected coefficient of elasticity upon being attached to finger grips of a hypodermic syringe barrel and extended as the hypodermic syringe barrel is drawn back within said sleeve and upon release, to propel the hypodermic syringe needle through said small opening into the patient at such velocity to be undetectable by patient.

* * * * *